US012758793B2

(12) United States Patent
Kuusela et al.

(10) Patent No.: US 12,758,793 B2
(45) Date of Patent: Oct. 13, 2026

(54) RADIATION TREATMENT PLAN OPTIMIZATION METHOD AND APPARATUS

(71) Applicant: Siemens Healthineers International AG, Steinhausen (CH)

(72) Inventors: Esa Kuusela, Espoo (FI); Tuomas Tallinen, Espoo (FI); Shahab Basiri, Siuntio (FI); Marko Rusanen, Espoo (FI); Mirko Myllykoski, Helsinki (FI)

(73) Assignee: Siemens Healthineers International AG, Steinhausen (CH)

( * ) Notice: Subject to any disclaimer, the term of this patent is extended or adjusted under 35 U.S.C. 154(b) by 474 days.

(21) Appl. No.: 18/368,163

(22) Filed: Sep. 14, 2023

(65) Prior Publication Data

US 2025/0090862 A1 Mar. 20, 2025

(51) Int. Cl.
*A61N 5/10* (2006.01)

(52) U.S. Cl.
CPC ........... *A61N 5/1031* (2013.01); *A61N 5/103* (2013.01); *A61N 5/1036* (2013.01); *A61N 5/1038* (2013.01); *A61N 5/1048* (2013.01); *A61N 5/1071* (2013.01)

(58) Field of Classification Search
CPC ........ A61N 103/1031; A61N 103/1036; A61N 103/1038; A61N 103/1048; A61N 103/1071; A61N 5/103; A61N 5/1031; A61N 5/1036; A61N 5/1038; A61N 5/1048
See application file for complete search history.

(56) References Cited

U.S. PATENT DOCUMENTS

| | | | | |
|---|---|---|---|---|
| 2020/0398080 A1* | 12/2020 | Ruokokoski | ......... | A61N 5/1031 |
| 2021/0299469 A1 | 9/2021 | Harju | | |
| 2022/0008748 A1 | 1/2022 | Huang | | |
| 2024/0189622 A1* | 6/2024 | Kuusela | ............... | A61N 5/1031 |
| 2026/0021326 A1* | 1/2026 | Kang | .................. | A61N 5/1067 |

FOREIGN PATENT DOCUMENTS

WO 2022200243 A1 9/2022

OTHER PUBLICATIONS

Extended European Search Report from related European Application No. 24194731.6; dated Feb. 10, 2025; 11 pages.
Bangert, Mark et al.; Comparison of beam angle selection strategies for intracranial IMRT; Med. Phys. 40(1) Jan. 2013; 011716-1 to 011716-11.

(Continued)

*Primary Examiner* — Mark R Gaworecki
(74) *Attorney, Agent, or Firm* — Fitch, Even, Tabin & Flannery LLP

(57) ABSTRACT

During a radiation treatment plan optimization loop, a control circuit can conduct a dosimetric optimization iteration to yield a dosimetric-based plan result and then conduct a non-dosimetric optimization iteration to yield a non-dosimetric-based plan result. The control circuit can then assess the dosimetric-based plan result and the non-dosimetric-based plan result to yield a convergence assessment result. The latter can then be taken into account when determining whether to conclude continued radiation treatment plan optimization loops.

16 Claims, 6 Drawing Sheets

(56) References Cited

OTHER PUBLICATIONS

Papp, Dávid et al.; A modular approach to intensity-modulated arc therapy optimization with nocoplanar trajectories; Abstract only; Physics in Medicine & Biology, 60(13), 2015, pp. 5179-5198. DOI 10.1088/0031-9155/60/13/5179.

Carreira-Perpiñán, Miguel Á. et al.; Distributed Optimization of Deeply Nested Systems; Appearing in Proceedings of the 17th International Conference on Artificial Intelligence and Statistics (AISTATS) 2014, Reykjavik, Iceland. JMLR: W&CP vol. 33.

Gabay, Daniel et al.; A Dual Algorithm for the Solution of Nonlinear Variational Problems via Finite Element Approximation; Comp. & Math. with Appls., vol. 2 (1976), pp. 17-40.

* cited by examiner

700

```
f_0 = create_initial_fluences()
s_0 = create_initial_control_points()
w_pf, w_ps = set_initial_penalty_strength()
i = 0
while not convergence(f,s, w_pf, w_ps):
        f_s = calculate_fluence(s_i)                                //actual fluence
        c_f = calculate_dosimetric_cost(f_i)
        c_pf = w_pf * fluence_norm(f_i, f_s)                        //penalty term
        grad_c_f = calculate_cost_gradient(c_f)
        grad_c_F += w_pf * grad_for_fluence_norm(f_i, f_s)      //cost gradient
        f_i+1 = f_i + gradient_descent_step(grad_c_f, f_i, f_s) //e.g. line search
        w_pf = update_penalty_for_fluence(w_pf, i, f, s)
        s_i+1 = update_candidate_control_point(s_i, f_i+1, w_ps)
        w_ps = update_penalty_for_control_points(w_ps, w_pf, I, f, s)
        i++
s_opt = s_i
```

FIG. 7

RADIATION TREATMENT PLAN OPTIMIZATION METHOD AND APPARATUS

TECHNICAL FIELD

These teachings relate generally to treating a patient's planning target volume with energy pursuant to an energy-based treatment plan and more particularly to optimizing an energy-based treatment plan.

BACKGROUND

The use of energy to treat medical conditions comprises a known area of prior art endeavor. For example, radiation therapy comprises an important component of many treatment plans for reducing or eliminating unwanted tumors. Unfortunately, applied energy does not inherently discriminate between unwanted material and adjacent tissues, organs, or the like that are desired or even critical to continued survival of the patient. As a result, energy such as radiation is ordinarily applied in a carefully administered manner to at least attempt to restrict the energy to a given target volume. A so-called radiation treatment plan often serves in the foregoing regards.

A radiation treatment plan typically comprises specified values for each of a variety of treatment-platform parameters during each of a plurality of sequential fields. Treatment plans for radiation treatment sessions are often partially or fully automatically generated through a so-called optimization process. As used herein, "optimization" will be understood to refer to improving a candidate treatment plan without necessarily ensuring that the optimized result is, in fact, the singular best solution. Such optimization often includes automatically incrementally adjusting one or more physical treatment parameters (often while observing one or more corresponding limits in these regards) and mathematically calculating a likely corresponding treatment result (such as a level of dosing) to identify a given set of treatment parameters that represent a good compromise between the desired therapeutic result and avoidance of undesired collateral effects.

Direct aperture optimization is an example of a radiation treatment plan optimization approach that typically aims for fast treatment delivery by directly modeling corresponding multi-leaf collimator segment shapes and weights. Unfortunately, direct aperture optimization can present a challenging optimization problem, at least in part, because this approach can include combining a computationally demanding dose evaluation task with an essentially combinatorial optimization of the leaf sequence (or other non-trivially coupled degrees-of-freedom consideration that corresponds to the behavior of the treatment platform during administration of the radiation treatment).

BRIEF DESCRIPTION OF THE DRAWINGS

The above needs are at least partially met through provision of the radiation treatment plan optimization method and apparatus described in the following detailed description, particularly when studied in conjunction with the drawings, wherein:

FIG. 7 presents pseudocode as configured in accordance with various embodiments of these teachings.

Figure 1:
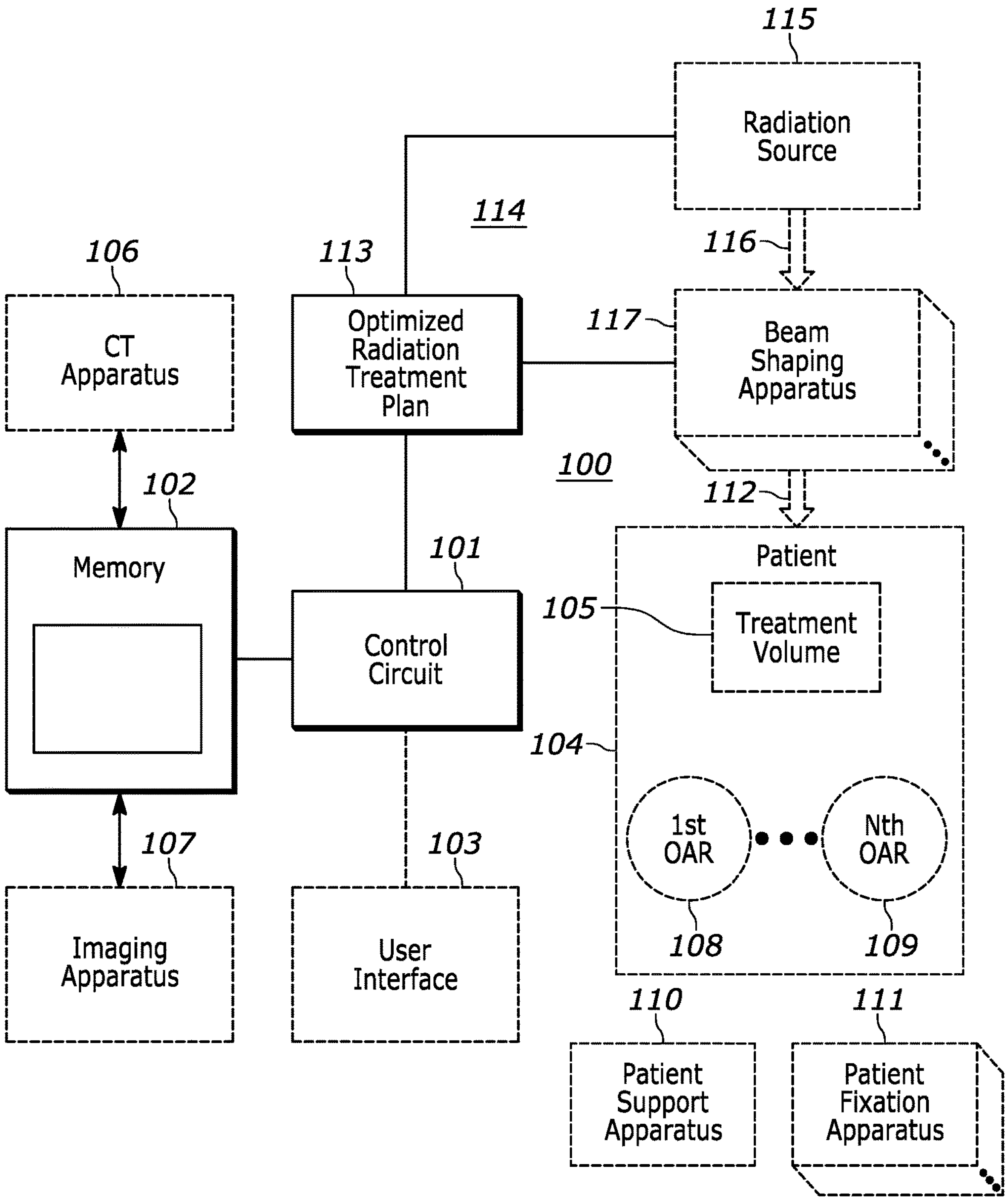
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, pursuant to these various embodiments and during a radiation treatment plan optimization loop, a control circuit conducts a dosimetric optimization iteration to yield a dosimetric-based plan result and then conducts a non-dosimetric optimization iteration to yield a non-dosimetric-based plan result. The control circuit then assesses the dosimetric-based plan result and the non-dosimetric-based plan result to yield a convergence assessment result. The latter can then be taken into account when determining whether to conclude continued radiation treatment plan optimization loops.

By one approach, the aforementioned dosimetric optimization iteration comprises an iterative operation to explore a fluence setting. By another approach, in lieu of the foregoing or in combination therewith, the aforementioned non-dosimetric optimization iteration comprises an iterative operation to explore at least one control point setting.

By one approach, during one or more subsequent radiation treatment optimization loops, these teachings will provide for conducting a subsequent dosimetric optimization iteration to yield a subsequent dosimetric-based plan result but not conducting a non-dosimetric optimization iteration to yield a subsequent non-dosimetric-based plan result. The control circuit can then assess the subsequent dosimetric-based plan result with respect to the non-dosimetric-based plan result (as previously determined) to yield a subsequent convergence assessment result. The control circuit can then determine whether to conclude continued radiation treatment plan optimization loops as a function, at least in part, of the subsequent convergence assessment result.

By one approach, assessing the dosimetric-based plan result and the non-dosimetric-based plan result to yield a convergence assessment result comprises, at least in part, applying an optimization penalty as a function of convergence assessment results that represent deviation between the dosimetric-based plan result and the non-dosimetric-based plan result.

By one approach, conducting the dosimetric optimization iteration to yield a dosimetric-based plan result can comprise, at least in part, conducting the dosimetric optimization iteration as a function, at least in part, of a previous interim result determined during a non-dosimetric optimization iteration.

In practice, these teachings will support a highly flexible and practical application setting. By one approach, for example, upon determining to conclude continued radiation treatment plan optimization loops, these teachings will accommodate then outputting an optimized radiation treatment plan. Therapeutic radiation can then be administered to the particular patient as a function, at least in part, of that optimized radiation treatment plan.

These and other benefits may become clearer upon making a thorough review and study of the following detailed description. Referring now to the drawings, and in particular to FIG. 1, an illustrative apparatus 100 that is compatible with many of these teachings will first be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information such as optimization information for a particular patient and information regarding a particular radiation treatment platform as described herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information.

In this illustrative example the control circuit 101 is configured to ultimately output an optimized energy-based treatment plan (such as, for example, an optimized radiation treatment plan 113). This energy-based treatment plan typically comprises specified values for each of a variety of treatment-platform parameters during each of a plurality of sequential exposure fields. In this case the energy-based treatment plan is generated through an optimization process, examples of which are provided further herein.

By one approach the control circuit 101 can operably couple to an energy-based treatment platform 114 that is configured to deliver therapeutic energy 112 to a corresponding patient 104 having at least one treatment volume 105 and also one or more organs-at-risk (represented in FIG. 1 by a first through an Nth organ-at-risk 108 and 109) in accordance with the optimized energy-based treatment plan 113. These teachings are generally applicable for use with any of a wide variety of energy-based treatment platforms/apparatuses. In a typical application setting the energy-based treatment platform 114 will include an energy source such as a radiation source 115 of ionizing radiation 116.

By one approach this radiation source 115 can be selectively moved via a gantry along an arcuate pathway (where the pathway encompasses, at least to some extent, the patient themselves during administration of the treatment). The arcuate pathway may comprise a complete or nearly complete circle as desired. By one approach the control circuit 101 controls the movement of the radiation source 115 along that arcuate pathway, and may accordingly control when the radiation source 115 starts moving, stops moving, accelerates, de-accelerates, and/or a velocity at which the radiation source 115 travels along the arcuate pathway.

As one illustrative example, the radiation source 115 can comprise, for example, a radio-frequency (RF) linear particle accelerator-based (linac-based) x-ray source. A linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical energy-based treatment platform 114 may also include one or more support apparatuses 110 (such as a couch) to support the patient 104 during the treatment session, one or more patient fixation apparatuses 111, a gantry or other movable mechanism to permit selective movement of the radiation source 115, and one or more energy-shaping apparatuses (for example, beam-shaping apparatuses 117 such as jaws, multi-leaf collimators, and so forth) to provide selective energy shaping and/or energy modulation as desired.

In a typical application setting, it is presumed herein that the patient support apparatus 110 is selectively controllable to move in any direction (i.e., any X, Y, or Z direction) during an energy-based treatment session by the control circuit 101. As the foregoing elements and systems are well understood in the art, further elaboration in these regards is not provided here except where otherwise relevant to the description.

Figure 2:
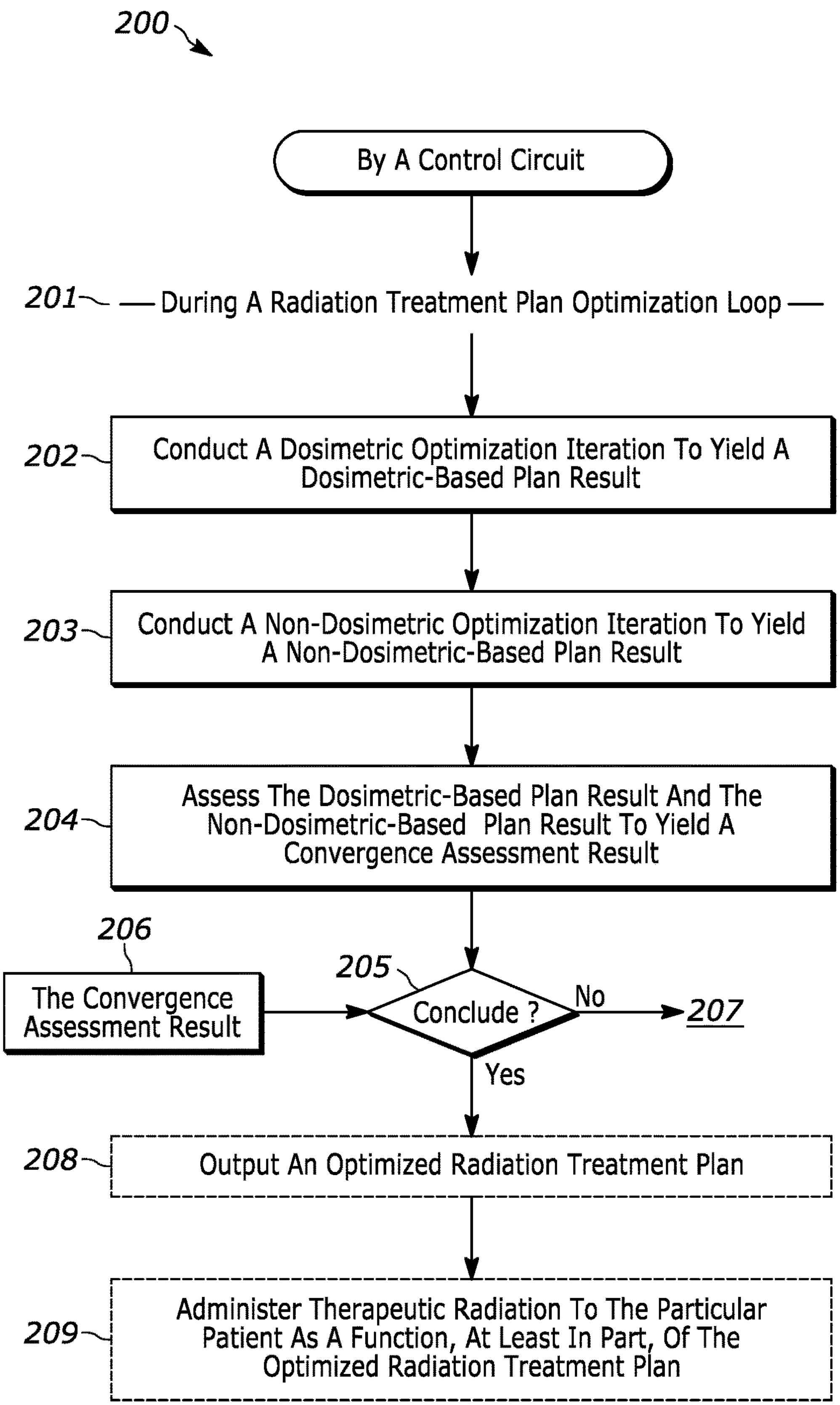
FIG. 2 comprises a flow diagram as configured in accordance with various embodiments of these teachings.

Referring now to FIG. 2, a process 200 that can be carried out, for example, in conjunction with the above-described application setting (and more particularly via the aforementioned control circuit 101) will be described. Generally speaking, this process 200 can serve to facilitate generating an optimized radiation treatment plan 113 to thereby facilitate treating a particular patient with therapeutic radiation using a particular radiation treatment platform 114 per that optimized radiation treatment plan 113.

This process 200 will be understood to take place during a single radiation treatment plan optimization loop as denoted by reference numeral 201.

At block 202, the control circuit conducts a dosimetric optimization iteration to yield a dosimetric-based plan result. These teachings will accommodate any of a variety of approaches in these regards. By one approach, the dosimetric optimization iteration comprises an iterative operation to explore a fluence setting. Fluence, of course, represents radiative flux integrated over time and comprises a fundamental metric in dosimetry (i.e., the measurement and calculation of an absorbed dose of ionizing radiation in matter and tissue). By one approach, if desired, this dosimetric optimization iteration can comprise, at least in part, conducting the dosimetric optimization iteration as a function, at least in part, of an interim result determined during a previous non-dosimetric optimization iteration. (By "previous," the foregoing can refer to a previous non-dosimetric optimization iteration that was conducted during the current optimization loop or that was conducted during a previous optimization loop for the current optimization exercise.)

At block 203, the control circuit conducts a non-dosimetric optimization iteration to yield a non-dosimetric-based plan result. These teachings will accommodate any of a variety of approaches in these regards. By one approach, this non-dosimetric optimization iteration comprises an iterative operation to explore at least one control point setting. Control points refer to specific positions or angles at which a radiation beam is turned on or off during treatment. Control points typically serve to help shape the radiation beam and to optimize the dose distribution to target the tumor while sparing surrounding healthy tissues.

At block 204, the control circuit 101 then assesses the dosimetric-based plan result and the non-dosimetric-based plan result to yield a convergence assessment result. By one approach, this assessment may comprise, at least in part, applying an optimization penalty as a function of convergence assessment results that represent deviation between the dosimetric-based plan result and the non-dosimetric-based plan result. For example, the greater that deviation, the greater the corresponding optimization penalty.

At decision block 205, the control circuit 101 then determines whether to conclude continued radiation treatment plan optimization loops as a function, at least in part, of the aforementioned convergence assessment result 206. When the control circuit 101 determines to continue with additional optimization loops at reference numeral 207, these teachings will accommodate various approaches. As one example, the control circuit 101 may repeat the foregoing steps 202-205 using at least one iterated variable. As another example, the control circuit 101 may utilize the process 300 that is described further below with respect to FIG. 3.

When determining to conclude continued radiation treatment plan optimization loops, at optional block 208 the control circuit 101 can output a corresponding optimized radiation treatment plan 113. At optional block 209, therapeutic radiation can then be administered to the particular patient 104 using the aforementioned treatment platform 114 as a function, at least in part, of that optimized radiation treatment plan 113.

Figure 3:
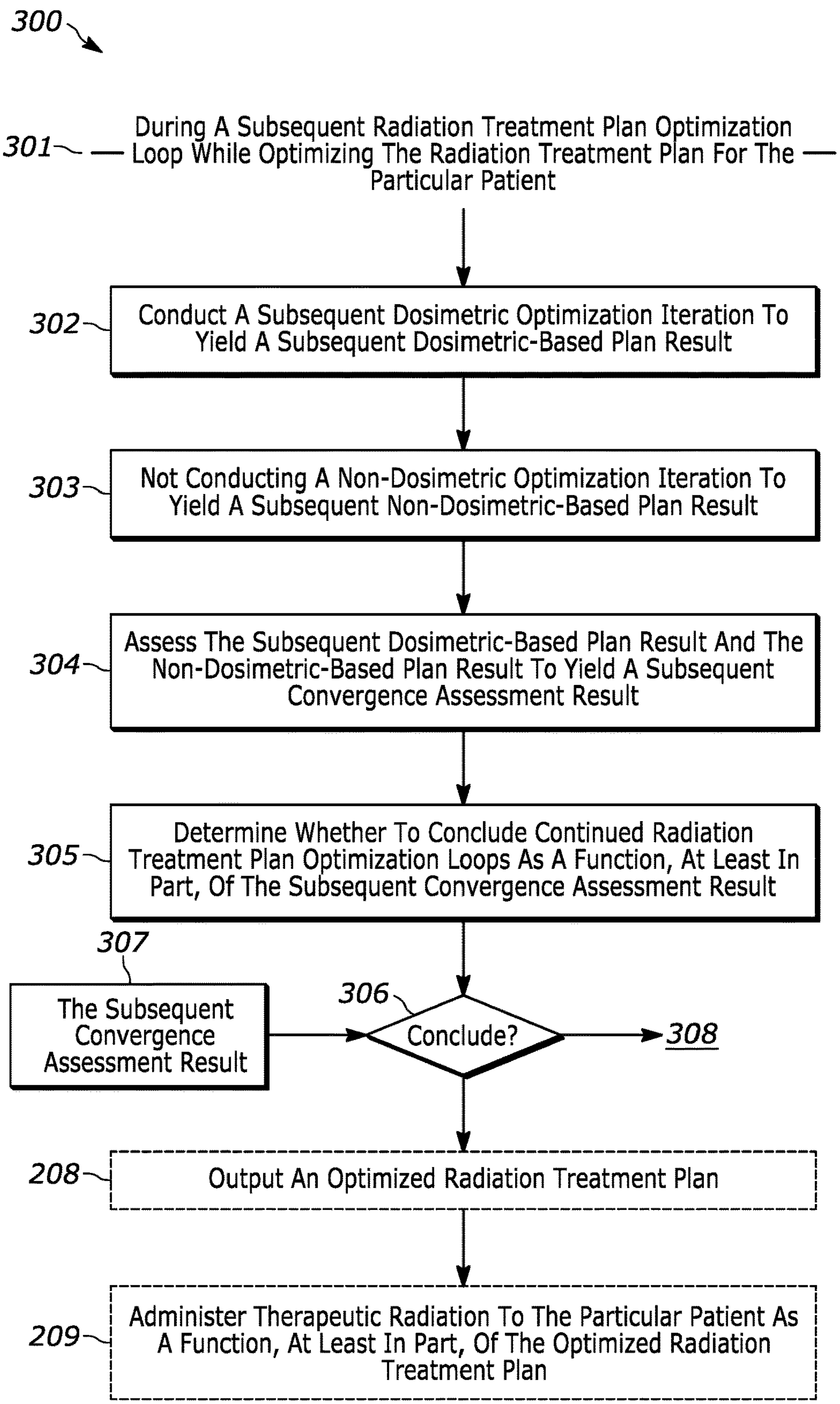
FIG. 3 comprises a flow diagram as configured in accordance with various embodiments of these teachings.

Referring now to FIG. 3, the aforementioned process 300 will be described. As indicated at reference numeral 301, this process 300 takes place during a subsequent radiation treatment plan optimization loop (i.e., a radiation treatment plan optimization loop that is subsequent to the loop that takes place in the above-described process 200 for FIG. 2.

At block 302, the control circuit 101 conducts a subsequent dosimetric optimization iteration to yield a subsequent dosimetric-based plan result.

Block 303 indicates that, unlike the aforementioned process 200, the control circuit 101 does not conduct a subsequent non-dosimetric optimization iteration to yield a subsequent non-dosimetric-based plan result. Instead, as described below, the control circuit 101 will reuse the previously yielded non-dosimetric-based plan result.

At block 304, the control circuit 101 then assesses the subsequent dosimetric-based plan result and the non-dosimetric-based plan result (i.e., a previous non-dosimetric-based plan result, which may be from a just-previous iteration loop, the loop before that, or possibly even further back in the overall process) to yield a subsequent convergence assessment result.

At decision blocks 305 and 306, the control circuit 101 then determines whether to conclude continued radiation treatment plan optimization loops as a function, at least in part, of the aforementioned subsequent convergence assessment result 307. As before, when the control circuit 101 determines to continue with additional optimization loops at reference numeral 308, these teachings will accommodate various approaches. As one example, the control circuit 101 may repeat the foregoing steps 202-205 or steps 302-306 using at least one iterated variable.

When determining to conclude continued radiation treatment plan optimization loops, and again as described earlier, at optional block 208 the control circuit 101 can output a corresponding optimized radiation treatment plan 113 and at optional block 209, therapeutic radiation can then be administered to the particular patient 104 using the aforementioned treatment platform 114 as a function, at least in part, of that optimized radiation treatment plan 113.

These teachings are both practical and flexible in practice and will accommodate a variety of supplemental and/or alternative features. Further details in such regards will now be provided, it being understood that the scope of these teachings is not to be viewed as being defined by or limited by such details.

The applicant has observed that direct aperture optimization is a challenging optimization problem, at least in part because the computationally demanding dose evaluation task is combined with the essentially combinatorial optimization of the leaf sequence (or other non-trivially coupled degrees-of-freedom feature(s) that determines treatment platform behavior during administration of a radiation treatment). The applicant has further observed that, while gradient-based optimization methods are powerful when applied to fluence-based optimization, it can be difficult and often impractical to calculate the gradient back to control-point space.

The direct aperture optimization type of radiation therapy plan creation is an optimization problem where the task is to solve $$s_{opt} = \operatorname*{argmin}_{s \in S'} c(s) \tag{1}$$

where $s_{opt}$ is the optimal control-point sequence that minimizes a cost function c(s) and which belongs to the set of feasible solutions S'. In practice, the cost function can be presented in a form $$c(s) = c_{tot}(c_f(D(F(s))), c_s(s)) \tag{2}$$

where a significant part of the computational effort of the cost function evaluation is related to the control-point sequence only through nested functions F and D (which represent the fluence calculation and fluence-based dose-calculation).

For the purposes of this description, $c_f$ represents the dosimetrical cost (i.e., a part that depends on the control-point sequence only through dose calculation), and $c_s$ represents the non-dosimetrical cost. $c_{tot}$ represents a function that combines these two cost terms and may comprise, for example, a weighted or unweighted sum.

The applicant posits that finding optimal solution for equation 2 above can be challenging because, at least in part, different parts of this chain of nested functions are quite different in their computational and mathematical properties. The applicant observes that, while dose function D(f) tends to be a linear smoothly-differentiable function of continuous fluence pixel vector values, the fluence calculation function F(s) is instead a non-convex function of a control-point sequence. Those differences render many prior art optimization strategies impractical. For example, gradient-based approaches may be efficient to find good solutions in fluence-space, but there may be little assurance that a feasible leaf sequence exists that could provide such a fluence map. Correspondingly, standard gradient-free combinatorial optimization schemes may not be able to efficiently evaluate the dosimetrical cost.

The present teachings will accommodate an approach where a control-point sequence can be optimized separately to optimal fluence maps, but where a deviation between these solutions is penalized:

$$(f_{opt}, s_{opt}) = \operatorname*{argmin}_{f;s \in S'} c_f(D(f)) + c_s(s) + w_p\|f - F(s)\|. \tag{3}$$

When $w_p$ is increased, the $s_{opt}$ of the previous formula can be presented as $$s_{opt} \approx \operatorname*{argmin}_{s \in S'} (c_f(D(F(s))) + c_s(s)), \tag{4}$$

meaning that the found solution in the mutual optimization approximates the solution of the original equation 1 above. (The nomenclatures of equations 3 and 4 are as follows: f denotes fluence maps and s the control-point sequence (or leaf sequence), $w_p$ is a scalar weight factor determining the strength of the penalty, $\|\cdot\|$ is some suitable norm (such as L2) to measure the difference between the two fluences, $c_f$ and $c_s$ denote the dosimetrical and non-dosimetrical cost terms (with the former depending on control points via dose calculation, and the latter not needing dose evaluation).

These teachings will accommodate changing optimization logic by not requiring that every intermediate state of the optimization process is actually presented by a feasible leaf-sequence. One can seek an optimal solution in fluence space and then try to find a leaf sequence that will actually create that same fluence. When the penalty strength w_p is gradually increased, the current candidate fluence will move closer and closer to the actual fluence of the candidate leaf sequence.

Figure 4:
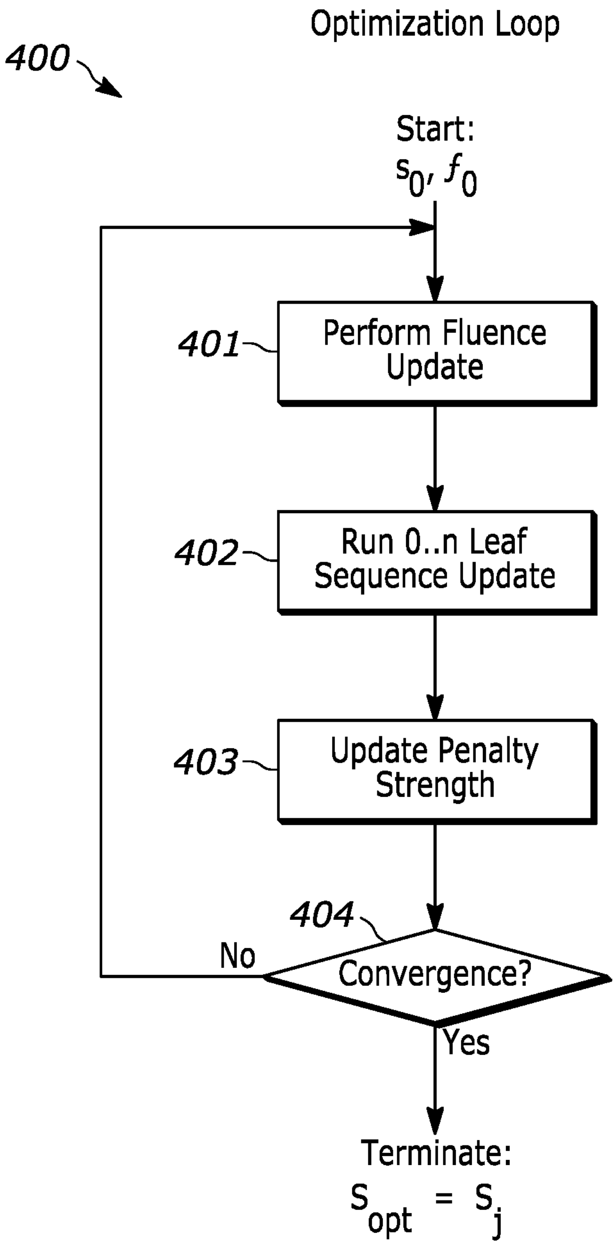
FIG. 4 comprises a flow diagram as configured in accordance with various embodiments of these teachings.

FIG. 4 presents a particular instantiation of these teachings in accordance with the foregoing description. In particular, FIG. 4 depicts an optimization loop 400.

Figure 5:
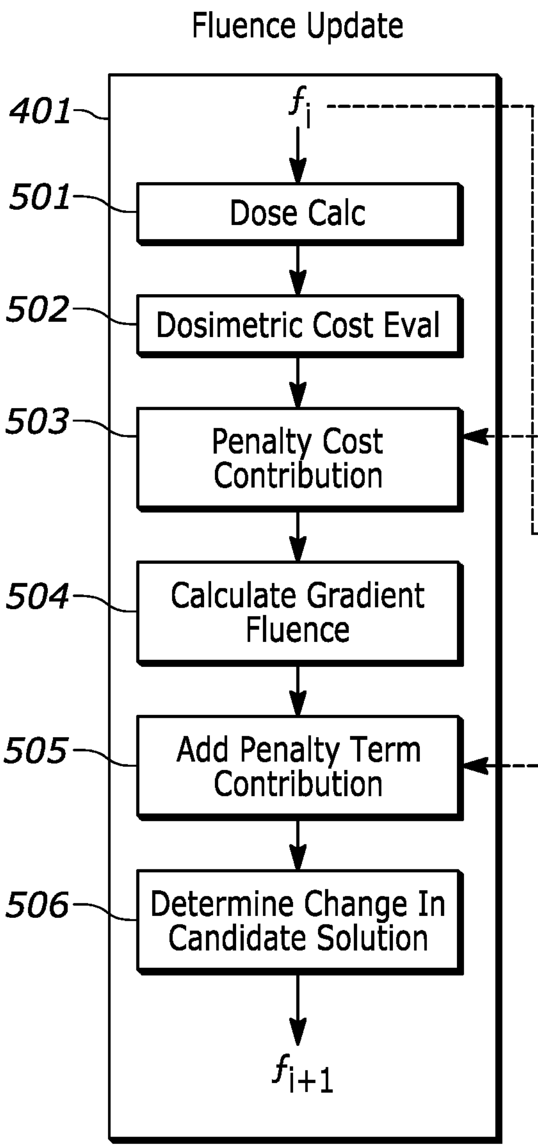
FIG. 5 comprises a flow diagram as configured in accordance with various embodiments of these teachings.

This loop 400 begins by performing a fluence update at block 401. FIG. 5 presents one approach in these regards. In this illustrative example the fluence update 401 begins at block 501 with a dose calculation followed by a dosimetric cost evaluation at block 502. The update then determines a penalty cost contribution at block 503 (which may be undertaken as a function, at least in part, of a previously-determined fluence calculation as described below). A gradient fluence is calculated at block 504 and at block 505 a penalty term contribution is added (where this calculation may also take into account the above noted fluence calculation). This fluence update then can conclude by determining any change in the candidate solution at block 506.

Figure 6:
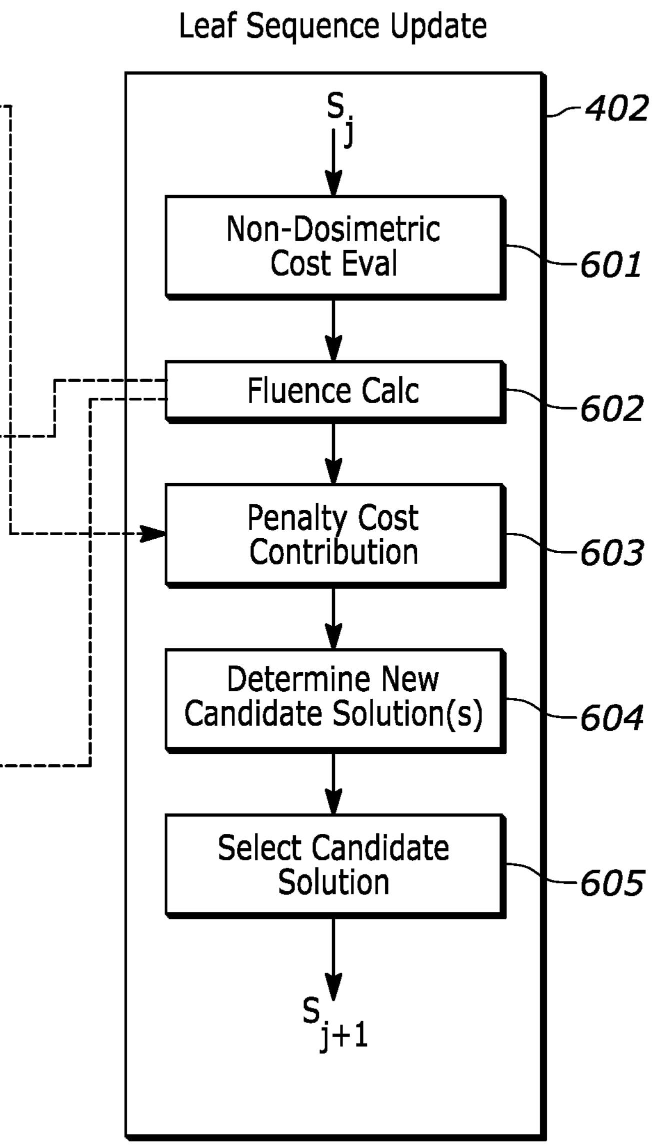
FIG. 6 comprises a flow diagram as configured in accordance with various embodiments of these teachings.

Returning to FIG. 4, at block 402 the leaf sequence update is run. Referring momentarily to FIG. 6, this update can begin at block 601 with a non-dosimetric cost evaluation followed by a fluence calculation at block 602. At block 603 a penalty cost contribution is undertaken (and may be informed by fluence information from the fluence update 401) and then, at block 604, a determination of one or more new candidate solutions. This illustrative update procedure concludes at block 605 with selection of a particular candidate solution.

Returning to FIG. 4, at block 403 the loop updates the penalty strength and then a decision made at block 404 regarding whether the solutions have sufficiently converged. When not yet true, the foregoing process can repeat. When true, the process can terminate.

FIG. 7 presents pseudocode 700 for implementing an approach that is consistent with the foregoing teachings.

So configured, it will be appreciated that, to at least a substantial extent, optimization in fluence-space and optimization in control-point space are decoupled. This helps to support greater flexibility in organizing the main optimization approach. For example, while the optimization is done in the fluence space, the solution space search can utilize the efficient gradient descent approach without reverting back at every iteration to a solution where a feasible leaf-sequence is also found. This makes it possible to evaluate approximatively achievable dosimetrical quality (for example, if the plan quality is defined with a set of clinical goals) without the need to find, for every intermediate state, a leaf-sequence that could actually generate the candidate fluences.

In a typical prior art approach, the search space in fluence optimization may potentially include solutions that violate the laws of physics (by including, for example, negative fluence values) or that may be practically impossible (for example, by including very large positive values). Hence, finding a feasible leaf-sequence at every iteration has been important to ensure that the optimizer remains in feasible fluence space. It will be appreciated that the present teachings will accommodate constraining searching in valid fluence space by embedding such a constraint in $c_f$, to thereby help avoid determining whether a feasible leaf-sequence in every iteration is unnecessary.

It will be appreciated that the present teachings do not require defining the control points from the beginning of the optimization. Instead, the fluence optimization could be performed solely based on a number of calculation directions. The optimum number of control points could then be defined afterwards based on the complexity of the leaf mutations needed for achieving the optimum fluence maps. Such resource allocations could be a part of the leaf sequencing optimization.

It should also be noted that these teachings will support having the iterations of the leaf-sequence optimization and the iterations of the fluence optimization performed in different intervals. For example, these teachings will support starting the optimizer with first focusing on finding a converging candidate fluence with w_p set to zero and only later starting to do leaf sequencing to thereby avoid situations where time is spent in searching candidate leaf sequences for sub-optimal dosimetrical solutions. By one approach, the penalty term (weighted by w_p) could be replaced by a fluence shape penalty that is purely a function of the fluence maps with the intention to penalize fluences that are, in general, difficult to reproduce efficiently with the anticipated beam-shaping/modulating elements (such as a multi-leaf collimator).

Those skilled in the art will recognize that a wide variety of modifications, alterations, and combinations can be made with respect to the above-described embodiments without departing from the scope of the invention, and that such modifications, alterations, and combinations are to be viewed as being within the ambit of the inventive concept.

What is claimed is:

1. A method to facilitate optimizing a radiation treatment plan for a particular patient, the method comprising:

by a control circuit and during a radiation treatment plan optimization loop:

conducting a dosimetric optimization iteration to yield a dosimetric-based plan result;

conducting a non-dosimetric optimization iteration to yield a non-dosimetric-based plan result;

assessing the dosimetric-based plan result and the non-dosimetric-based plan result to yield a convergence assessment result;

determining whether to conclude continued radiation treatment plan optimization loops as a function, at least in part, of the convergence assessment result.

2. The method of claim 1 wherein the dosimetric optimization iteration comprises an iterative operation to explore a fluence setting.

3. The method of claim 1 wherein the non-dosimetric optimization iteration comprises an iterative operation to explore at least one control point setting.

4. The method of claim 1 further comprising, during a subsequent radiation treatment plan optimization loop while optimizing the radiation treatment plan for the particular patient:

conducting a subsequent dosimetric optimization iteration to yield a subsequent dosimetric-based plan result;

not conducting a non-dosimetric optimization iteration to yield a subsequent non-dosimetric-based plan result;

assessing the subsequent dosimetric-based plan result and the non-dosimetric-based plan result to yield a subsequent convergence assessment result;

determining whether to conclude continued radiation treatment plan optimization loops as a function, at least in part, of the subsequent convergence assessment result.

5. The method of claim 1, wherein assessing the dosimetric-based plan result and the non-dosimetric-based plan result to yield a convergence assessment result comprises, at least in part, applying an optimization penalty as a function of convergence assessment results that represent deviation between the dosimetric-based plan result and the non-dosimetric-based plan result.

6. The method of claim 1, wherein conducting the dosimetric optimization iteration to yield a dosimetric-based plan result comprises, at least in part, conducting the dosimetric optimization iteration as a function, at least in part, of an interim result determined during a non-dosimetric optimization iteration.

7. The method of claim 1 further comprising:

when determining to conclude continued radiation treatment plan optimization loops, outputting an optimized radiation treatment plan.

8. The method of claim 7, further comprising:

administering therapeutic radiation to the particular patient as a function, at least in part, of the optimized radiation treatment plan.

9. An apparatus to facilitate optimizing a radiation treatment plan for a particular patient, the apparatus comprising:

a control circuit configured to, during a radiation treatment plan optimization loop:

conduct a dosimetric optimization iteration to yield a dosimetric-based plan result;

conduct a non-dosimetric optimization iteration to yield a non-dosimetric-based plan result;

assess the dosimetric-based plan result and the non-dosimetric-based plan result to yield a convergence assessment result;

determine whether to conclude continued radiation treatment plan optimization loops as a function, at least in part, of the convergence assessment result.

10. The apparatus of claim 9 wherein the dosimetric optimization iteration comprises an iterative operation to explore a fluence setting.

11. The apparatus of claim 9 wherein the non-dosimetric optimization iteration comprises an iterative operation to explore at least one control point setting.

12. The apparatus of claim 9 wherein the control circuit is further configured, during a subsequent radiation treatment plan optimization loop while optimizing the radiation treatment plan for the particular patient, to:

conduct a subsequent dosimetric optimization iteration to yield a subsequent dosimetric-based plan result;

not conduct a non-dosimetric optimization iteration to yield a subsequent non-dosimetric-based plan result;

assess the subsequent dosimetric-based plan result and the non-dosimetric-based plan result to yield a subsequent convergence assessment result;

determine whether to conclude continued radiation treatment plan optimization loops as a function, at least in part, of the subsequent convergence assessment result.

13. The apparatus of claim 9, wherein the control circuit is configured to assess the dosimetric-based plan result and the non-dosimetric-based plan result to yield a convergence assessment result by, at least in part, applying an optimization penalty as a function of convergence assessment results that represent deviation between the dosimetric-based plan result and the non-dosimetric-based plan result.

14. The apparatus of claim 9, wherein the control circuit is configured to conduct the dosimetric optimization iteration to yield a dosimetric-based plan result by, at least in part, conducting the dosimetric optimization iteration as a function, at least in part, of an interim result determined during a non-dosimetric optimization iteration.

15. The apparatus of claim 9 wherein the control circuit is further configured to:

upon determining to conclude continued radiation treatment plan optimization loops, output an optimized radiation treatment plan.

16. The apparatus of claim 15, wherein the control circuit is further configured to:

administer therapeutic radiation to the particular patient as a function, at least in part, of the optimized radiation treatment plan.

* * * * *